US00PP36389P2

(12) United States Plant Patent
Hogan

(10) Patent No.: US PP36,389 P2
(45) Date of Patent: Jan. 14, 2025

(54) ***CHOISYA* PLANT NAMED 'Valencia Fizz'**

(50) Latin Name: ***Choisya* x *hybrida***
Varietal Denomination: Valencia Fizz

(71) Applicant: Sean B. Hogan, Portland, OR (US)

(72) Inventor: Sean B. Hogan, Portland, OR (US)

( * ) Notice: Subject to any disclaimer, the term of this patent is extended or adjusted under 35 U.S.C. 154(b) by 0 days.

(21) Appl. No.: 18/438,396

(22) Filed: Feb. 9, 2024

(51) Int. Cl.
*A01H 5/02* (2018.01)
*A01H 6/78* (2018.01)

(52) U.S. Cl.
USPC ..... Plt./226

(58) Field of Classification Search
USPC ..... Plt./226, 263.1
CPC ..... A01H 5/02; A01H 5/00; A01H 6/78
See application file for complete search history.

(56) References Cited

PUBLICATIONS

Plant Haven, Inc. PlantHaven Hot Selection—California Spring Trials 2023 Video, retrieved on Jun. 17, 2024 at https://planthaven.com/2023/04/planthaven-hot-selection-california-spring-trials-2023-video/, 3 pp. (Year: 2023).*

Oregon State University Landscape Plants *Choisya x dewitteana* 'Aztec Pearl' retrieved on Sep. 24, 2024 at https://landscapeplants.oregonstate.edu/plants/choisya-dewitteana-aztec-pearl, 2 pp. (Year: 2024).*

* cited by examiner

*Primary Examiner* — June Hwu
(74) *Attorney, Agent, or Firm* — Weatherly IP Solutions, LLC; James M. Weatherly

(57) ABSTRACT

A new cultivar of *Choisya* plant named 'Valencia Fizz' that is characterized by its naturally branching spherical dense plant habit with short internodes and numerous basal and lateral branches. The foliage of 'Valencia Fizz' is dense and dark green in color when mature and exhibits orange blossom fragrance. The newly emerging foliage of 'Valencia Fizz' is lighter green-yellow in color. The flowers of 'Valencia Fizz' are borne in many compound corymbs, and are very numerous and relatively large for the genus and its varieties. The flowers of 'Valencia Fizz' are pleasantly sweetly fragrant, reminiscent of orange blossom. The flowers of 'Valencia Fizz' are rotate and bear five rotate free petals. 'Valencia Fizz' blooms profusely in May to August and sporadically in early and mid-spring and in late summer.

2 Drawing Sheets

Genus and species: *Choisya* x *hybrida*.
Variety denomination: 'Valencia Fizz'.

BACKGROUND OF THE NEW PLANT

The present invention relates to a new and distinct cultivar of the genus *Choisya*. *Choisya* plants are compact shrubs bearing trifoliate leaves (*Choisya ternata*) or palmate fan-like leaves (*Choisya dumosa, Choisya arizonica*) which are fragrant when crushed. The flowers of all species of *Choisya* are white and pleasantly fragrant, reminiscent of the scent of orange blossom. A common name for *Choisya* is Mexican Orange Blossom.

The new cultivar 'Valencia Fizz' is a complex hybrid known botanically as *Choisya* x *hybrida* and will be referred to hereinafter by the cultivar name 'Valencia Fizz'.

The inventor selected 'Valencia Fizz' in 2011 from seedlings raised by the inventor within a *Choisya* breeding program commenced in 2003. The inventor raised seedlings from seed resulting from the controlled pollination of the species *Choisya dumosa* (unpatented) as male parent and a female parent which itself was a hybrid of *Choisya arizonica* 'Whetstone' (patent status unknown) and *Choisya dewitteana* 'Aztec Pearl' (patent status unknown).

The most commonly grown species and varieties of *Choisya* are plants of *Choisya ternata* which bears dark green trifoliate compound leaves. The three species *dumosa, arizonica, dewitteana* involved in the hybridization of 'Valencia Fizz' all bear long and narrow fimbriated foliage. The inventor selected 'Valencia Fizz' for the compactness (short internodes) of its fine textured compound leaves, and the profuse production of large white flowers. These characteristics recommend 'Valencia Fizz' as a hedging plant and as an attractive shrub for the landscape and garden, or for growing in containers.

The inventor asexually reproduced 'Valencia Fizz' in 2011 by the method of softwood cuttings. Since that time, the unique characteristics of the new *Choisya* plant have been uniform, stable and reproduced true to type in successive generations of asexual reproduction.

SUMMARY

The following traits have been repeatedly observed and represent the characteristics of the new *Choisya* cultivar 'Valencia Fizz'. 'Valencia Fizz' has not been tested under all possible conditions and phenotypic differences may be observed with variations in environmental, climatic and cultural conditions, however, without any variance in genotype.

1. 'Valencia Fizz' exhibits a naturally branching spherical dense plant habit with short internodes and numerous basal and lateral branches.
2. After one year of growth in a 2-gallon container, plants of 'Valencia Fizz' achieve a height and diameter of 45 cm.

3. A mature plant of 'Valencia Fizz' which is growing in-ground achieves a height and diameter of 1 m.
4. The foliage of 'Valencia Fizz' is dense and dark green in color when mature. The foliage of 'Valencia Fizz' is light green, or green-yellow, when newly emerging. The foliage of 'Valencia Fizz' exhibits orange blossom fragrance, particularly when crushed.
5. The flowers of 'Valencia Fizz' are borne in compound corymbs, and are very numerous and relatively large for the genus and its varieties. The flowers are sweetly orange-blossom fragrant.
6. The petals of the flowers of 'Valencia Fizz' are rotate and five in number.
7. 'Valencia Fizz' flowers profusely in May to August and sporadically in early and mid-spring and in late summer.
8. 'Valencia Fizz' requires growing in well-drained soils and positioning in full sun to partial shade.
9. 'Valencia Fizz' is hardy at least to USDA Zone 7.
10. 'Valencia Fizz' will maintain its natural dense compact habit when pruned after each season's flowering.

BRIEF DESCRIPTION OF THE PHOTOGRAPHS

The accompanying color photographs illustrate the overall appearance of the new *Choisya* variety 'Valencia Fizz' showing colors as true as it is reasonably possible to obtain in colored reproductions of this type. Colors in the photographs may differ from the color values cited in the detailed botanical description, which accurately describe the actual colors of the new variety 'Valencia Fizz'.

Figure 1:
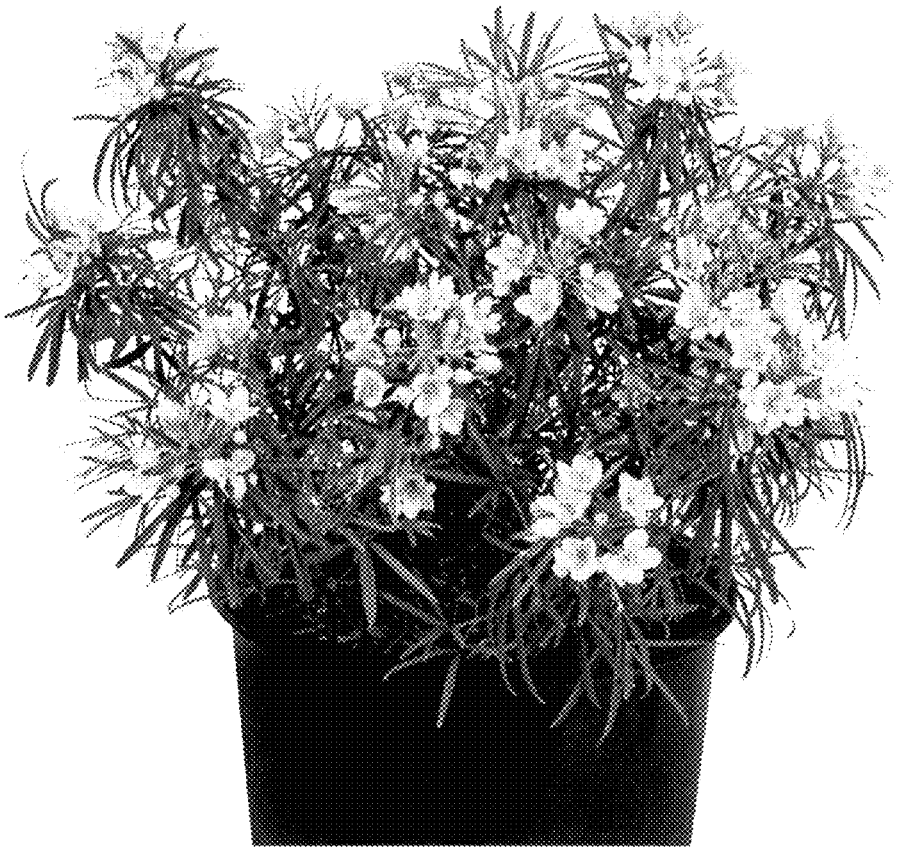
FIG. 1 depicts a one-year-old plant of 'Valencia Fizz' in flower and growing out of doors in Portland, Oregon.
Figure 2:
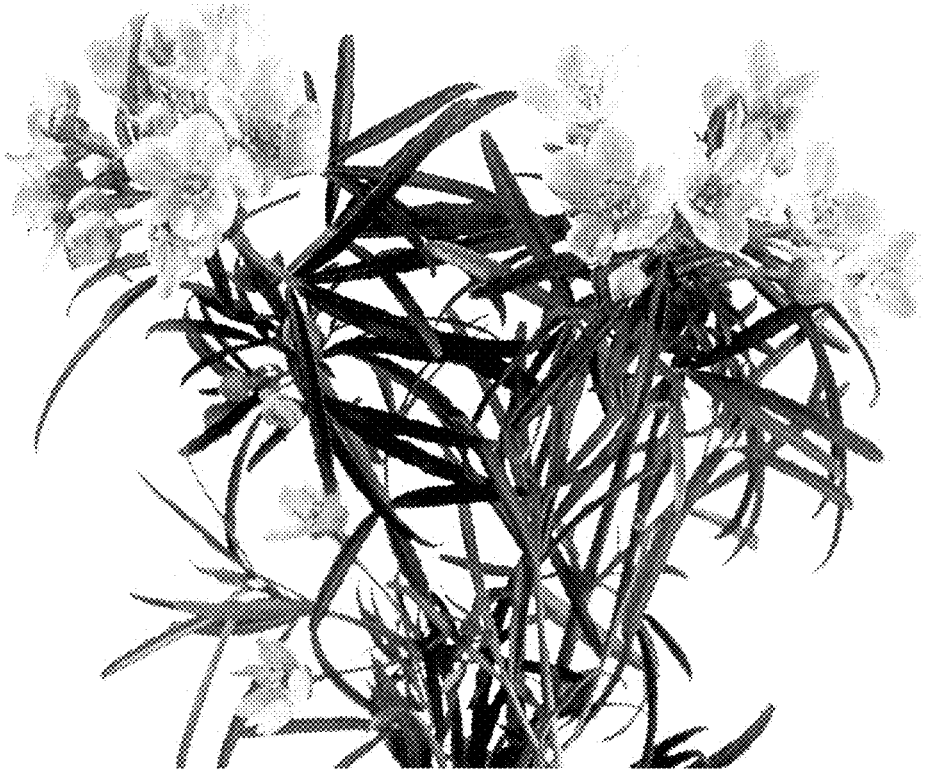
FIG. 2 depicts a close-up view of the foliage and inflorescences of 'Valencia Fizz'.

Photographs were taken in April 2022 in Santa Barbara, California from one-year-old plants which were growing outdoors in 2-gallon containers. No chemicals were used to treat the plants. All photographs were made using conventional techniques and although colors may appear different from actual colors due to light reflectance they are as accurate as possible by conventional photography.

BOTANICAL DESCRIPTION OF THE PLANT

The following is a detailed description of the new cultivar 'Valencia Fizz'. Data was collected in April 2022 from one-year-old plants grown in 2-gallon containers in Santa Barbara, California. The color determinations are in accordance with the 2007 edition of The Colour Chart of The Royal Horticultural Society, London, England, except where general color terms of ordinary dictionary significance are used. No chemicals were used to treat the plants. Growing conditions are typical of other *Choisya*.

Botanical classification: *Choisya*.
- *Variety*.—'Valencia Fizz'.
- *Species*.—X *hybrida*.
- *Family*.—Rutaceae.

Parentage:
- *Male parent*.—Unnamed plant of the species *Choisya dumosa*.
- *Female parent*.—Plant raised by the inventor from the open pollination of *Choisya arizonica* 'Whetstone' and *Choisya dewitteana* 'Aztec Pearl'.

Plant description:
- *Growth habit*.—Spherical.
- *Use*.—In containers, as a hedging plant, and in the landscape.
- *Suitable container sizes*.—1-gallon to 3-gallon.
- *Dimensions at one year of age* (*the observed plants*).—Height and diameter 45 cm.
- *Dimensions at two years of age*.—Height and diameter 60 cm.
- *Dimensions* (*mature plant established in ground*).—Height and diameter of 1 m.
- *Hardiness*.—At least hardy to USDA Zone 7.
- *Propagation*.—Stem cuttings taken and rooted in summer.
- *Time to initiate roots*.—10 to 12 weeks are required to produce roots on an initial cutting.
- *Crop time*.—One year to produce a finished one-gallon container from a rooted cutting.
- *Root system*.—Fibrous.
- *Light*.—Plant in full sun or partial shade.
- *Soil*.—Plant in moist but well drained soil.
- *Type*.—Deciduous shrub.
- *Seasonal interest*.—Finely textured dense foliage year-round and profuse fragrant flowering in summer. Pruning after flowering encourages dense plant habit and more profuse flowering in the following season.

Basal stem (below first pinching or stropping):
- *Shape*.—Terete.
- *Dimensions*.—8 cm in length, 6 mm in diameter at soil level.
- *Color*.—N199D.
- *Surface*.—Rough, glabrous, lenticels N199C.

Branches:
- *Branching arrangement*.—Approximately 20 basal and lateral stems arise from base and basal stem after pinching or stopping. Some basal stems originate from the root system as suckers.
- *Branch stem dimensions*.—30 cm in length, 5 mm to 15 mm in diameter.
- *Branch stem shape*.—Terete.
- *Internode distance*.—4 mm.
- *Stem color*.—N199D.

Foliage:
- *Leaf type, quantity per plant*.—Compound. 50 compound leaves.
- *Leaflet quantity, arrangement*.—Each compound leaf consists of 5 or 6 leaflets arranged fan-like and spaced approximately 5 mm above each other.
- *Leaf shape*.—Long, narrowly elliptic, adaxially concave.
- *Leaf division*.—Simple.
- *Leaf attachment*.—Sessile.
- *Leaf dimensions*.—Up to 10 cm in length and 1 cm in width.
- *Leaf surface* (*adaxial*).—Glabrous.
- *Leaf surface* (*abaxial*).—Slightly rough to the touch, glabrous.
- *Leaf texture*.—Leathery.
- *Leaf color* (*adaxial*).—139A (mature foliage), N144C (juvenile foliage).
- *Leaf color* (*abaxial*).—153A.
- *Leaf apex*.—Acute.
- *Leaf base*.—Cuneate.
- *Leaf margin*.—Minutely serrate.
- *Leaf venation pattern*.—Pinnate.

*Veins color* (*adaxial surface, mature foliage*).—Prominent midrib, slightly depressed, color 139B, lighter than mature foliage color.

*Veins color* (*adaxial surface, juvenile foliage*).—Prominent midrib and lateral veins, raised approximately 1 mm, color 143C, darker than juvenile foliage color.

*Lateral veins color* (*both surfaces*).—As adjacent leaf surface color.

Inflorescence:

*Inflorescence form*.—Compound corymb present at each leaf axil.

*Inflorescence quantity*.—12-15 inflorescences per one-year-old plant.

*Inflorescence dimensions*.—35 mm in length.

*Quantity of flowers per inflorescence*.—At peak, 6 open flowers and 4-6 developing and opening buds.

*Time and duration of flowering*.—Beginning in late April or early May according to climate and season, profuse during May to August, continuing into late summer.

*Position*.—Borne on peduncles arising from upper axillary nodes.

*Arrangement of flowers*.—Corymbs of branching pedicels along peduncle, secondary pedicel branching along primary pedicels.

*Inflorescence dimensions overall*.—50 mm to 65 mm in length or height, 24 mm to 55 mm in diameter.

*Peduncles*.—Shape: Terete. Color: N134B. Surface: Smooth, glabrous, semi-glossy.

*Bud*.—Shape: Elongated ovoid. Color: 157D.

*Calyx*.—Funnelform, adpressed to petal abaxial surfaces.

*Calyx dimensions*.—8 mm-12 mm in diameter, 4 mm-5 mm in height.

*Sepals*.—Quantity: 4 or 5 in number, basally fused. Dimensions: 5 mm in length, 4 mm in width. Sepal apex: Rounded. Sepal base: Truncate. Sepal color (adaxial surface): 151D, tinged 179C towards base. Sepal color (abaxial surface): 151D. Sepal surface (both surfaces): Lightly pubescent, hairs short, fine, color NN155B.

*Flowers*.—Quantity, aspect: Single, rotate, outward and upward facing. Dimensions: 30 mm in diameter, 5 mm in height. Pollinators: Attractive to bees. Attachment: Pedicellate. Pedicel shape: Terete. Pedicel dimensions: 40 mm-60 mm in length, 1 mm-2 mm in diameter. Pedicel surface: Smooth, glabrous, semi-glossy. Pedicel color: 149C.

*Petals*.—Quantity per flower, arrangement: Five, rotate, free bases overlapping. Petal shape: Elliptic. Petal dimensions: 20 mm in length, 10 mm in width. Petal apex: Acute. Petal base: Cuneate. Petal margin: Smooth, entire, wavy, upwardly concave. Petal colors: Adaxial surface N155D, abaxial surface N155D.

Reproductive organs:

*Number of stamens*.—18.

*Filament dimensions*.—2 mm in length and less than 0.5 mm in diameter.

*Filament color*.—1B.

*Anther shape*.—Bilobed, kidney-shaped.

*Anther dimensions*.—7 mm in length and 5 mm in width.

*Anther color*.—22A

*Pollen color*.—23C.

*Pollen amount*.—Moderate.

*Number of pistils*.—1 short pistil (less than 5 mm in length) per flower.

*Style*.—Terete, 8 mm-9 mm in length and 0.5 mm in diameter.

*Style color*.—150C.

*Style surface*.—Glabrous.

*Stigma shape*.—Capitate, globose (3 lobed).

*Stigma dimensions*.—1.5 mm-2 mm in length, less than 0.75 mm. in diameter.

*Stigma color*.—144D.

*Ovary shape*.—Ovoid.

*Ovary color*.—150A.

Fruit:

*Shape*.—Flattened spherical, leathery surface, contains 2-6 capsules.

Seed: Sparse (observed in spring), ovoid 1 mm in length, light brown in color.

Susceptibility to diseases: In common with varieties and species of the genus *Choisya*, 'Valencia Fizz' is susceptible to diseases associated with damp and cold growing and planting conditions, including grey mould (*Botrytis cinerea*), and root rot fungi. Plants which are grown in well-drained soil and in good sun are generally unaffected by these diseases.

Susceptibility to pests: Susceptible to common horticultural pests including aphids (*Aphidoidea*), red spider mite (*Tetranychus urticae*) in hot dry summers, and to leaf grazing gastropods, slugs and snails.

COMPARISON OF 'VALENCIA FIZZ' WITH ITS PARENTS

The species of the parents *Choisya dumosa, Choisya arizonica* and *Choisya dewitteana*, all bear long narrow leaves which are sparsely arranged within the plants. In comparison, the leaves of 'Valencia Fizz' are fine and borne on more basal and lateral branches so that the appearance of 'Valencia Fizz' is more dense and less open. In addition, the greater number of branches and leaf axils in plants of 'Valencia Fizz' give rise to more numerous inflorescences and flowers.

COMPARISON OF 'VALENCIA FIZZ' WITH OTHER KNOWN VARIETIES OF *CHOISYA*

Other varieties of *Choisya* known to the inventor include the involved parents *Choisya arizonica* 'Whetstone' and *Choisya dewittenana* 'Aztec Pearl' whose plant habits are more loose and open than the denser plant habit of 'Valencia Fizz'. In addition, varieties of *Choisya ternata* are common in commerce and are markedly different in bearing trifoliate compound leaves with elliptical leaflets. One variety *Choisya ternata* 'LICH' is widely grown and marketed as a golden-yellow foliaged sport of *Choisya ternata*.

I claim:

1. A new and distinct cultivar of *Choisya* Plant Named 'Valencia Fizz' as described and illustrated herein.

* * * * *